(12) United States Patent
Poulsen et al.

(10) Patent No.: US 11,617,920 B2
(45) Date of Patent: Apr. 4, 2023

(54) RESPIRATORY DEVICE AND SYSTEM FOR EXERCISING AND ANALYZING RESPIRATION OF A USER

(71) Applicant: Aerofit.dk ApS, Birkerød (DK)

(72) Inventors: Christian Tullberg Poulsen, Birkerød (DK); Tue Toft, København (DK); Rudy Bergholdt, Helsinge (DK); Klaus Karkov, Græsted (DK); Bjarne Månsson, Fredensborg (DK); Karsten Videbæk, Jyllinge (DK)

(73) Assignee: AIROFIT A/S, Copenhagen (DK)

( * ) Notice: Subject to any disclaimer, the term of this patent is extended or adjusted under 35 U.S.C. 154(b) by 1032 days.

(21) Appl. No.: 16/316,927

(22) PCT Filed: Jul. 13, 2017

(86) PCT No.: PCT/EP2017/067735
§ 371 (c)(1),
(2) Date: Jan. 10, 2019

(87) PCT Pub. No.: WO2018/011358
PCT Pub. Date: Jan. 18, 2018

(65) Prior Publication Data
US 2019/0299055 A1    Oct. 3, 2019

(30) Foreign Application Priority Data

Jul. 13, 2016 (DK) .............................. PA201600421
Feb. 24, 2017 (DK) .............................. PA201770139

(51) Int. Cl.
*A63B 23/18* (2006.01)
*A61B 5/091* (2006.01)
(Continued)

(52) U.S. Cl.
CPC .............. *A63B 23/18* (2013.01); *A61B 5/091* (2013.01); *A61B 5/097* (2013.01); *A61B 5/224* (2013.01);
(Continued)

(58) Field of Classification Search
CPC ......... A61B 5/091; A61B 5/097; A61B 5/224; A61B 5/682; A61B 2562/047;
(Continued)

(56) References Cited

U.S. PATENT DOCUMENTS 4,221,381 A    9/1980   Ericson
4,739,987 A    4/1988   Nicholson
(Continued)

FOREIGN PATENT DOCUMENTS

CA      2948137 A1     11/2015
EP      3141289 A1 *    3/2017   ........ A61M 16/0045
(Continued)

*Primary Examiner* — Gary D Urbiel Goldner
(74) *Attorney, Agent, or Firm* — Dinsmore & Shohl LLP

(57) ABSTRACT

The present disclosure relates to a respiratory system for exercising and analysing respiration of a subject comprising: a breathing unit comprising: a mouthpiece connected to: at least one inhalation air way, at least one exhalation air way, and an electronic sensor unit comprising at least one pressure gauge for measuring air pressure in the mouthpiece, and a processing unit for collecting/storing and/or transmitting air pressure data.

25 Claims, 7 Drawing Sheets

(51) Int. Cl.
*A61B 5/097* (2006.01)
*A61B 5/22* (2006.01)
*A63B 24/00* (2006.01)
*A63B 71/06* (2006.01)
*A61M 16/04* (2006.01)
*A63B 21/00* (2006.01)
*A61B 5/00* (2006.01)
*A61M 16/08* (2006.01)
*A63B 21/008* (2006.01)
*A61M 16/20* (2006.01)
*A61M 16/00* (2006.01)

(52) U.S. Cl.
CPC .......... *A61B 5/682* (2013.01); *A61M 16/049* (2014.02); *A61M 16/0858* (2014.02); *A61M 16/0866* (2014.02); *A63B 21/00069* (2013.01); *A63B 21/0088* (2013.01); *A63B 23/185* (2013.01); *A63B 24/0062* (2013.01); *A63B 71/0622* (2013.01); *A61B 2562/0247* (2013.01); *A61M 16/208* (2013.01); *A61M 2016/0027* (2013.01); *A61M 2205/3561* (2013.01); *A61M 2205/3592* (2013.01); *A61M 2205/502* (2013.01); *A61M 2205/8206* (2013.01); *A63B 2024/0068* (2013.01); *A63B 2024/0093* (2013.01); *A63B 2071/0658* (2013.01); *A63B 2071/0675* (2013.01); *A63B 2220/13* (2013.01); *A63B 2220/56* (2013.01); *A63B 2220/62* (2013.01); *A63B 2220/833* (2013.01); *A63B 2225/20* (2013.01); *A63B 2225/50* (2013.01); *A63B 2225/52* (2013.01); *A63B 2230/405* (2013.01)

(58) Field of Classification Search
CPC ........ A61B 21/00058; A61B 21/00069; A61B 21/00076; A61B 21/008; A61B 21/0085; A61B 21/0088; A61B 21/22; A61B 21/4027; A61B 21/4039; A61B 23/18; A61B 23/185; A61B 24/0062; A61B 24/0087; A61B 2024/0068; A61B 2024/0093; A61B 71/0619; A61B 71/0622; A61B 2071/0658; A61B 2071/0675; A61B 2209/08; A61B 2220/10; A61B 2220/13; A61B 2220/50; A61B 2220/56; A61B 2220/58; A61B 2220/62; A61B 2220/80; A61B 2220/83; A61B 2220/833; A61B 2225/20; A61B 2225/30; A61B 2225/50; A61B 2225/52; A61B 2230/40; A61B 2230/405; A61B 2230/42; A61B 2230/425; A61M 16/049; A61M 16/0858; A61M 16/0866; A61M 16/208; A61M 2016/0027; A61M 2205/3561; A61M 2205/3592; A61M 2205/502; A61M 2205/8206
See application file for complete search history.

(56) References Cited

U.S. PATENT DOCUMENTS

| | | | |
|---|---|---|---|
| 7,108,659 | B2 | 9/2006 | Ross et al. |
| 8,590,533 | B2 | 11/2013 | Danford |
| 8,915,247 | B2 | 12/2014 | Chalvignac et al. |
| 2003/0234017 | A1 | 12/2003 | Pelerossi et al. |
| 2008/0053452 | A1* | 3/2008 | Brown ............ A63B 21/00069 128/207.12 |
| 2008/0053456 | A1* | 3/2008 | Brown ............ A61M 16/0006 600/529 |
| 2009/0199853 | A1* | 8/2009 | Cegla .................. A63B 23/18 128/207.14 |
| 2012/0272956 | A1* | 11/2012 | Rusher ............... A61M 16/209 128/205.24 |
| 2016/0038056 | A1 | 2/2016 | Johnson et al. |
| 2016/0120462 | A1 | 5/2016 | Tunnell et al. |
| 2016/0150998 | A1 | 6/2016 | Shiner et al. |
| 2019/0299055 | A1* | 10/2019 | Poulsen ................ A61B 5/091 |

FOREIGN PATENT DOCUMENTS

| | | |
|---|---|---|
| JP | H07167694 A | 7/1995 |
| JP | H08164225 A | 6/1996 |
| JP | 2010518911 A | 6/2010 |
| JP | 2011182826 A | 9/2011 |
| JP | 2012187292 A | 10/2012 |
| WO | WO-2015120435 A1 | 8/2015 |
| WO | WO-2015/171097 A1 | 11/2015 |

* cited by examiner

System Components:

Device      Communication      Cloud Server

System Functions:

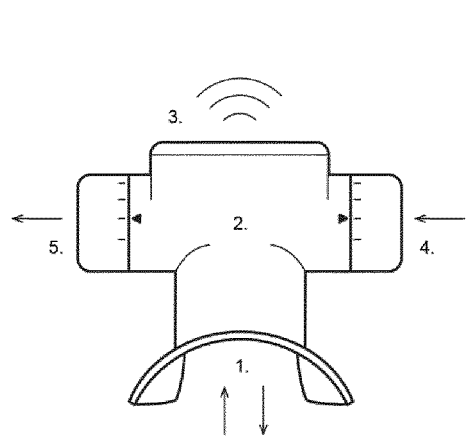
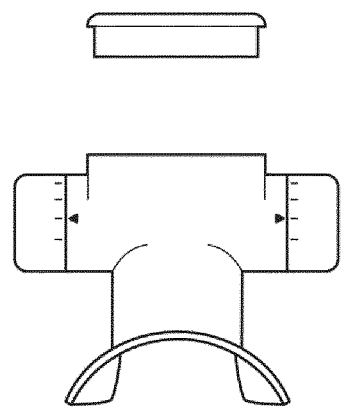
FIG. 3A  FIG. 3B
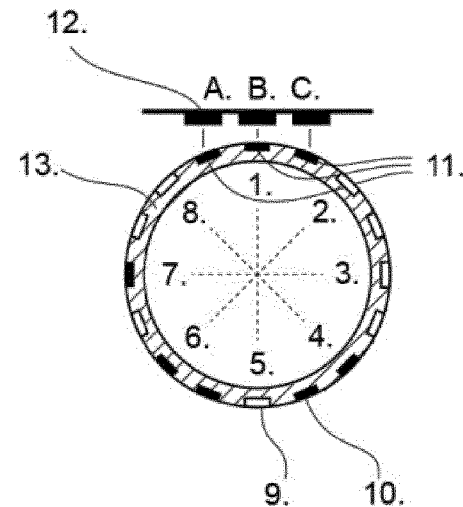
FIG. 5
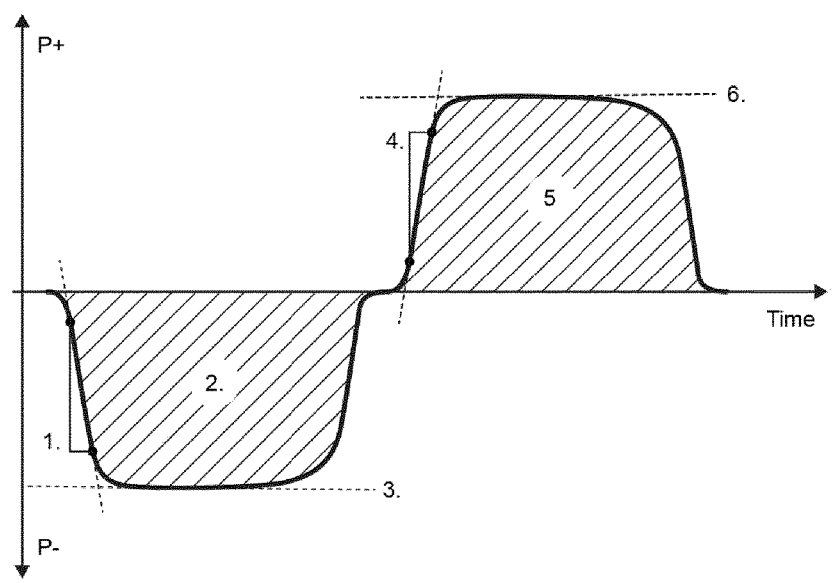
FIG. 6

RESPIRATORY DEVICE AND SYSTEM FOR EXERCISING AND ANALYZING RESPIRATION OF A USER

CROSS-REFERENCE TO RELATED APPLICATIONS

This application is the U.S. national stage of PCT/EP2017/067735 filed Jul. 13, 2017, which claims priority of Application No. DK PA201770139 filed Feb. 24, 2017 and Application No. DK PA201600421, filed Jul. 13, 2016; each of which is hereby incorporated by reference in its entirety.

The present disclosure relates to a respiratory device and a respiratory system for analyzing and improving the physical abilities of and through the respiratory system.

BACKGROUND OF INVENTION

Respiratory exercisers typically comprise a mouthpiece with adjustable air resistance to inhalation and exhalation.

In U.S. Pat. No. 4,221,381 the adjustment structure is regulating the size of at least one of the openings therein to control the size of the access opening to atmosphere. The air resistance is the same for both inhalation and exhalation.

In U.S. Pat. No. 4,739,987 two openings regulate the inhalation and exhalation resistance by the use of an aperture in each of two partitions which cover the openings to be brought into and out of alignment.

In U.S. Pat. No. 8,590,533 multiple air inlet inserts are provided for interchangeable use in the air inlet, allowing different rates and resistance to air flow.

In WO 2015/120435 a porous or non-porous material is making the air way resistance on both inhalation and exhalation.

In WO 2015/171097 adjustable throttles are used for making the air way resistance.

Respiratory analyzers typically comprise measurement and computation modules for analyzing the respiratory data.

In U.S. Pat. No. 7,108,659 air way resistances are by fixed apertures. The device comprises a flow rate meter and a computation module. Analyzed results include respiratory frequency and exercise duration.

These prior art devices and systems are associated with a number of inconveniences and problems which may be overcome by the presently disclosed respiratory system.

In particular the known devices are limited in relation to the feedback that is given to the user, in relation to the control of the resistance, in relation to the mechanical implementation of the device and in relation to measurements.

SUMMARY OF INVENTION

The present disclosure relates, in a first aspect, to a respiratory device and system for exercising and analysing respiration of a subject. A first embodiment of the presently disclosed respiratory system for exercising and analysing respiration of a subject comprises:
 a breathing unit comprising:
  a mouthpiece connected to:
   at least one inhalation air way,
   at least one exhalation air way, and
   an electronic sensor unit comprising:
    at least one pressure gauge for measuring air pressure in the mouthpiece, and
    a processing unit for collecting/storing and/or transmitting air pressure data.

In the preferred embodiment the adjustable inhalation air flow resistance and the adjustable exhalation air flow resistance are separate and configured to operate independently of each other, such that inhalation air flow resistance can be controlled independently—and can be different—from the exhalation air flow resistance. The electronic sensor unit may further comprise a wireless transmitter for continuously transmitting air pressure data in real-time.

The respiratory system may further comprise a software application executable on a remote device and configured for executing the steps of:
 continuously receiving said air pressure data via a receiver on the remote device,
 processing the air pressure data by means of the remote device to provide real-time breathing data representing inhaled air pressure, inhaled air flow rate, exhaled air pressure, exhaled air flow rate and one or more of: inhaled respiratory tract volume, exhaled respiratory tract volume, inhaled respiratory muscle strength, exhaled respiratory muscle strength, inhaled respiratory muscle explosive strength and exhaled respiratory muscle explosive strength,
 displaying at least a part of the real-time breathing data on a screen of the remote device, and
 comparing real-time breathing data to stored breathing data of a predefined personal breathing routine.

One aspect of the respiratory device and system relates to an adjustable resistance for inhalation and exhalation, and in particular that the least one inhalation air way has an adjustable inhalation air flow resistance, and the at least one exhalation air way has an adjustable exhalation air flow resistance. Respiratory training has a better effect when inhalation and exhalation exercise parameters can be individually adjusted and combined with real time monitoring and guidance on respiratory training exercise. Therefore the presently disclosed system has in a first embodiment been developed to comprise a breathing device with individually adjustable air flow resistances on inhaled and exhaled air.

It is a further advantage if individually adjustable air flow resistances on inhaled and exhaled air can be monitored by the system. Therefore, the breathing unit may further comprise sensors for separately reading the positions of the adjustable inhalation air flow resistance and adjustable exhalation air flow resistance. In one embodiment the sensors are magnetic sensors and the adjustable inhalation air flow resistance and adjustable exhalation air flow resistance are provided with magnets. The magnetic sensors may be provided outside a circular circumference of the flow resistance setting turn buttons, thereby indicating a position of a magnet on the turn button. The position of the turn buttons can thereby be indicated to the system.

A further aspect of the present disclosure relates to the electronic sensor unit being detachable from the breathing unit. A problem with the known devices is that they cannot be efficiently cleaned in for example a water bath since the device comprises electronics. By designing the device such that the electronic components are arranged in a detachable electronic sensor unit, the breathing unit can be removed and the rest of the breathing unit, i.e. the housing, mouthpiece, airways etc., can be cleaned separately without risk of damaging electronic components. The electronic sensor unit may be a cassette accommodating all electronic parts of the breathing unit.

These and other aspects of the invention are set forth in the following detailed description if the invention.

DESCRIPTION OF DRAWINGS

FIGS. 3A-B show an embodiment of the presently disclosed breathing unit having two individually adjustable air flow resistances.

FIG. 5 shows an embodiment of the reading of air flow resistance positions.

FIG. 6 shows the pressure as a function of time for a breathing scenario. From the measurement of air flow resistance, respiratory air pressure and time, a number of respiratory related data can be derived.

The drawings are exemplary and are intended to illustrate some of the features of the presently disclosed respiratory device and system for exercising and analysing respiration of a subject, and are not to be construed as limiting to the presently disclosed invention.

DETAILED DESCRIPTION OF THE INVENTION

The present disclosure relates to a respiratory device and a system for exercising and analysing respiration of a subject. The respiratory device comprises a breathing unit. The technical details of the breathing may refer to the breathing unit for itself or as a part in the respiratory system.

A first embodiment of the presently disclosed respiratory system for exercising and analysing respiration of a subject comprises a breathing unit comprising:
- a mouthpiece connected to:
  - at least one inhalation air way,
  - at least one exhalation air way,
  - at least one pressure gauge for measuring air pressure in the mouthpiece.

The system also comprises a wireless transmitter for continuously transmitting air pressure data in real-time. Such a wireless transmitter is preferably mounted in a detachable electronic sensor unit.

The system may further comprise a software application executable on a remote device and configured for executing the steps of: receiving said air pressure data via a receiver on the remote device, processing the air pressure data, displaying at least a part of the real-time breathing data on a screen of the remote device, and optionally comparing real-time breathing data to stored breathing data of a predefined personal breathing routine.

It is an objective of the invention to provide an incentive to the user to improve his or her ventilation. An electronic module may be comprised in the device to determine respiratory data of the subject. The electronic module can determine exercise parameters such as exercise duration, and data may be stored in a memory for future access and/or data can be transmitted to the software application and stored and/or processed on the remote device, or in the cloud. The electronic module can thus preferably communicate settings and data with software on for example a PC, tablet and smartphone, and/or a cloud based server. It is a further object to provide an electronic respiratory exerciser and analyzer that facilitates an improvement to both sport training exercises, sing training exercises, lung disease rehabilitation, etc.

An electronic sensor unit may be incorporated to measure exercise session data, such as air pressure, time, duration and air flow resistance settings. This enables the user to instantly optimize the exhalation and inhalation during the exercise session.

Figure 1:
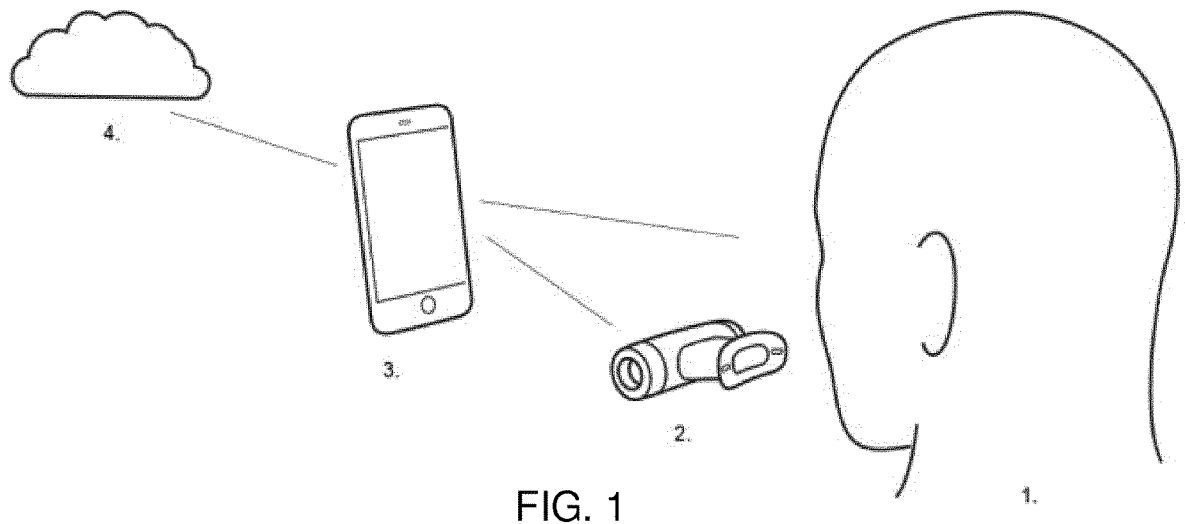
FIG. 1 shows an overview of the presently disclosed respiratory system for exercising and analysing respiration of a subject.

A software application executable on a remote device, or any calculation unit, may be used to calculate respiratory related data, such as flow rate, tract volume and respiratory muscle strength. The application may further analyze and return analysis of respiratory condition such as breathing patterns, max air pressure, and explosive force. This enables the user to correct the breathing pattern for the next exercise session. The application may also, based on the analysis, recommend exercise sessions for the improvement of the respiratory condition. The recommendation is provided to various exercise profiles. This enables the user to make long term improvements on the respiratory condition. FIG. 1 shows the general concept of the presently disclosed respiratory system for exercising and analysing respiration of a subject.

Figure 2:
FIG. 2 shows system components and system functions of the presently disclosed respiratory system for exercising and analysing respiration of a subject.
Figure 2:
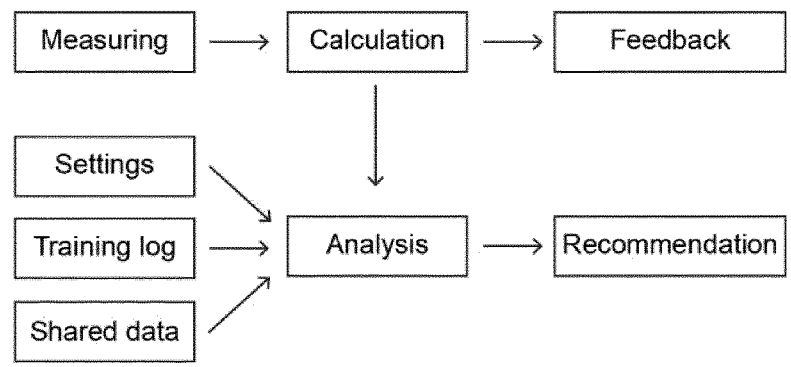

FIG. 2 shows the main components of an embodiment of the system. The system may comprises a breathing unit, preferably with individually adjustable air flow resistances on inhaled and exhaled air. The breathing unit holds an electronic sensor unit which measures exercise session data, such as air pressure, and/or time, and/or duration and/or air flow resistance settings. The electronic sensor unit may in one embodiment store the measured data locally. The unit may also perform some local calculations including respiratory related data such as flow rate, respiratory tract volume and respiratory muscle strength. Exercise data storage, data analyzing, session recommendations, and setup can be located both on the system itself and/or on a connected platform.

Breathing Unit

In one embodiment the breathing unit comprises a housing where the resistance units are located opposite each other, i.e. at opposite ends of the housing. The mouthpiece is attached to the housing between the resistance units and the electronic sensor unit is attached to the housing opposite the mouthpiece. When a user has the mouthpiece in the mouth and inhales, air is drawn through the inhalation air way where a one-way inhalation valve is configured to ensure that air can only be drawn in. When the user exhales air is blown through the exhalation air way where another one-way exhalation valve is configured to ensure that air can only be blown out. Hence, when the user inhales the exhalation one-way valve blocks the exhalation air way and when the user exhales the inhalation one-way valve blocks the inhalation air way. The separate resistance units provides for individually controllable inhalation and exhalation resistances, because in different training or treatment scenarios, it is important to be able to optimize either the inhalation resistance or the exhalation resistance.

A narrow air-way pressure channel may advantageously be provided in the device housing between the two resistance units. The longitudinal extension of the air-way pressure channel is preferably in substantially the same direction as the breathing of the user, i.e. in extension of the mouthpiece as also exemplified in FIG. 4D and also preferably centered with respect to the center of the mouthpiece. At least one air pressure gauge is located in direct fluid connection with this air-way pressure channel, preferably located at the end of the channel as exemplified in FIG. 4D. The air pressure gauge is located in the electronic unit. With this spatial configuration of the air-way pressure channel and the air pressure gauge the most correct air pressure measurements representing the user's inhalation and exhalation is provided because there is a direct fluid communication between the mouthpiece and the narrow air-way pressure channel.

The two one-way valves located in the breathing unit to ensure inhalation and exhalation through the two different resistance units may be identical. With the appropriate arrangement in the breathing unit it can be ensured that one of the one-way valves open during inhalation and close during exhalation, whereas the other one-way valve close during inhalation but open during exhalation, as also exemplified in FIG. 4D.

Figure 4A:
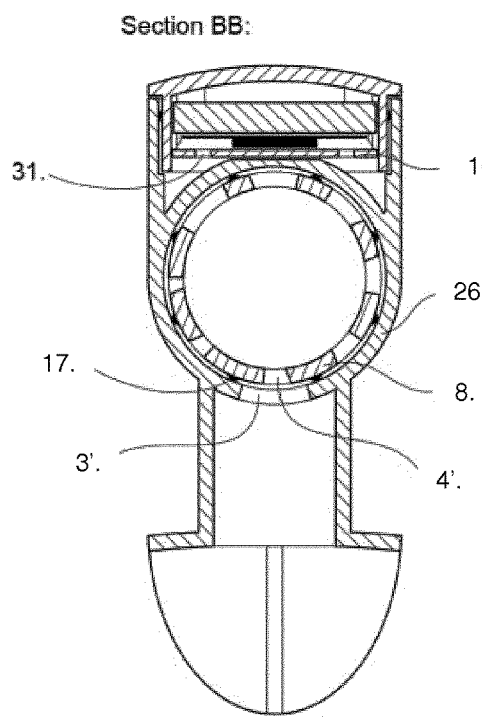
FIGS. 4A-D show different cross-sectional views of one embodiment of the presently disclosed breathing unit where FIG. 4A corresponds to the view along the line BB in FIG. 4D and FIG. 4B corresponds to the view along the line AA in FIG. 4D.
Figure 4B:
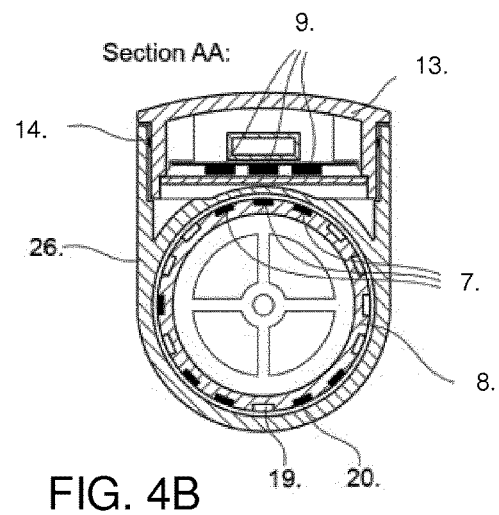
Figure 4C:
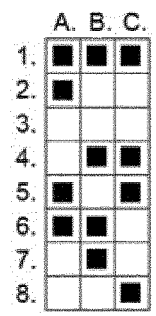
Figure 4D:
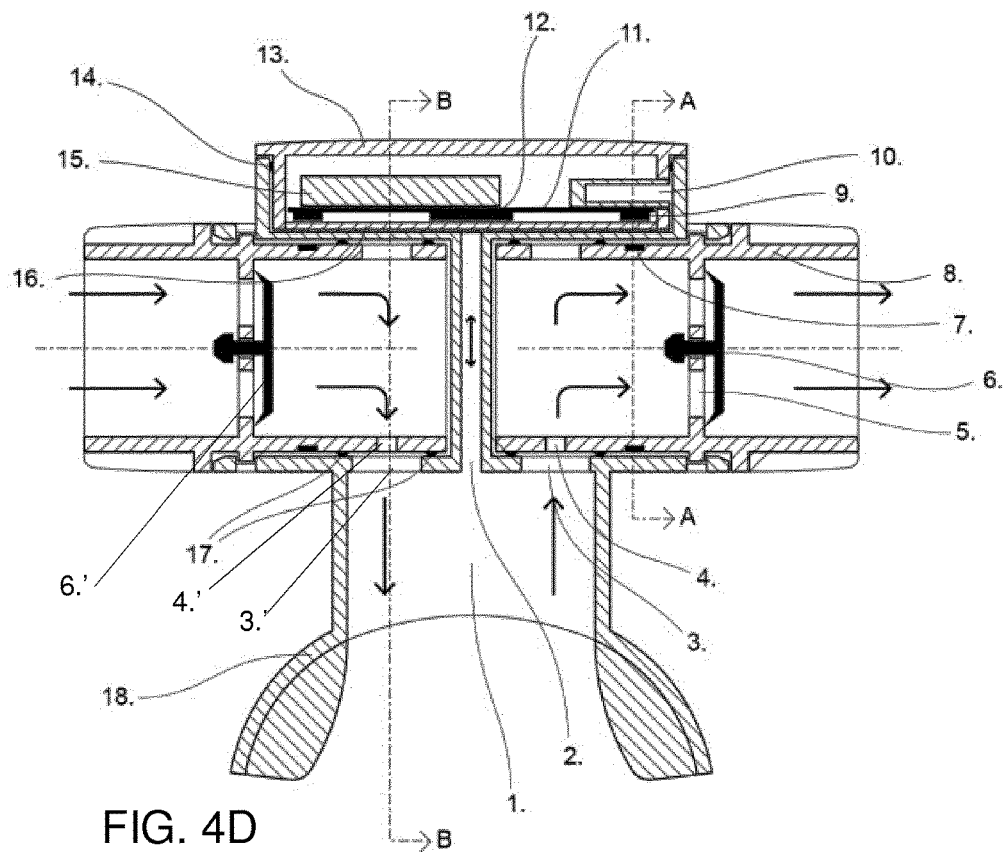
Figure 7A:
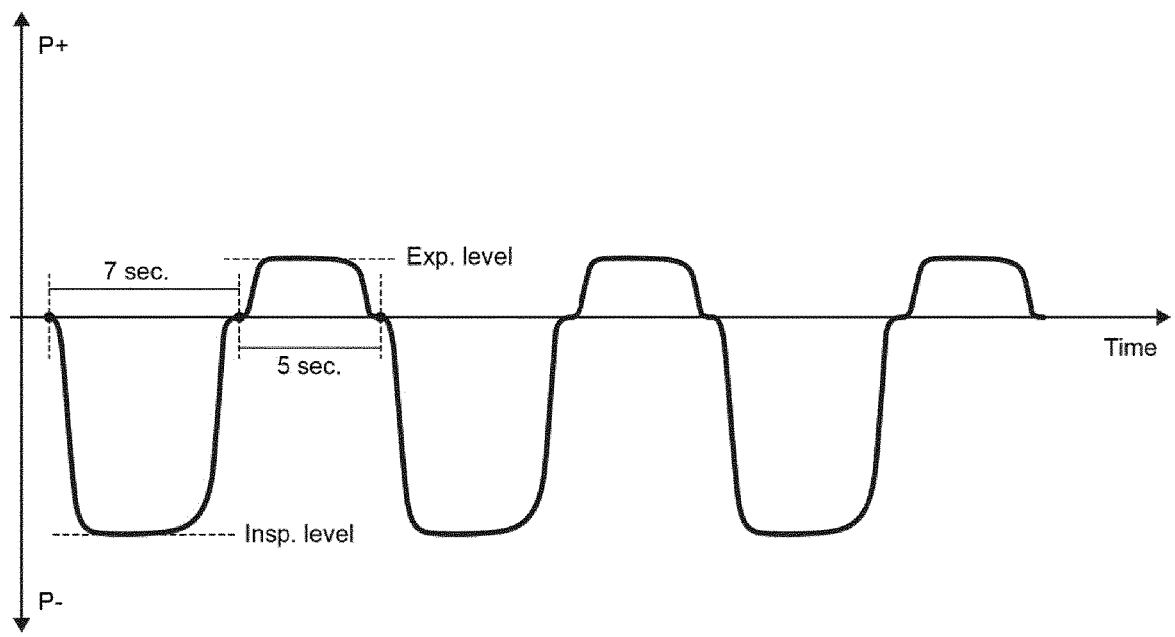
FIGS. 7A-F show examples of breathing patterns.
Figure 7B:
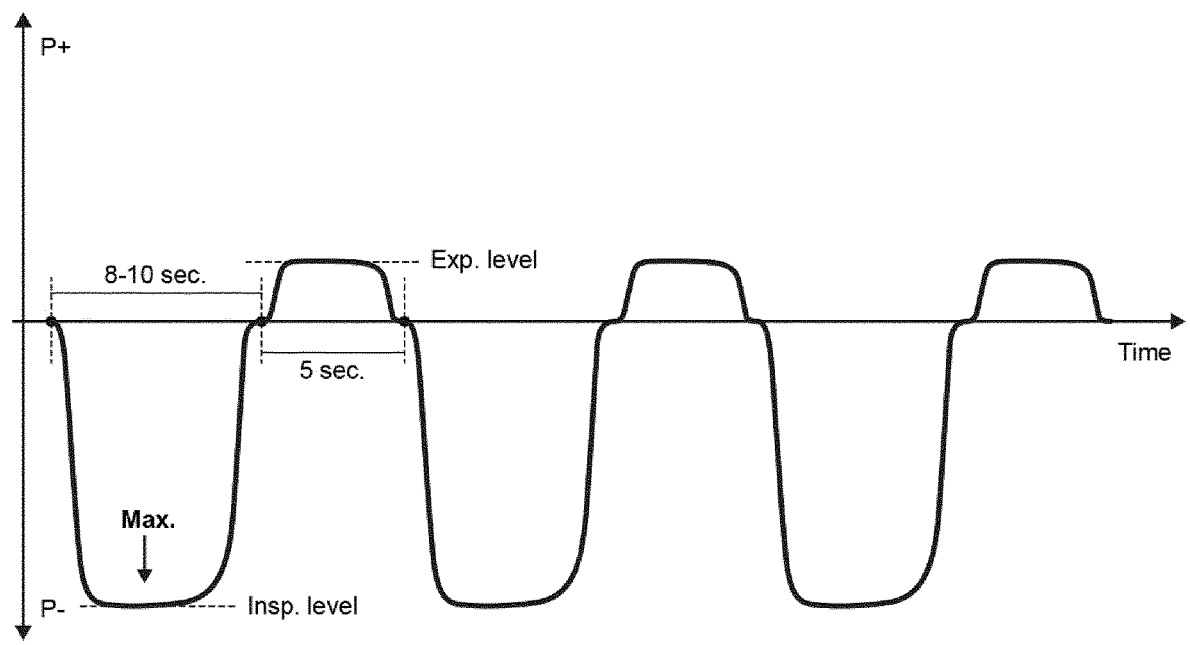
Figure 7C:
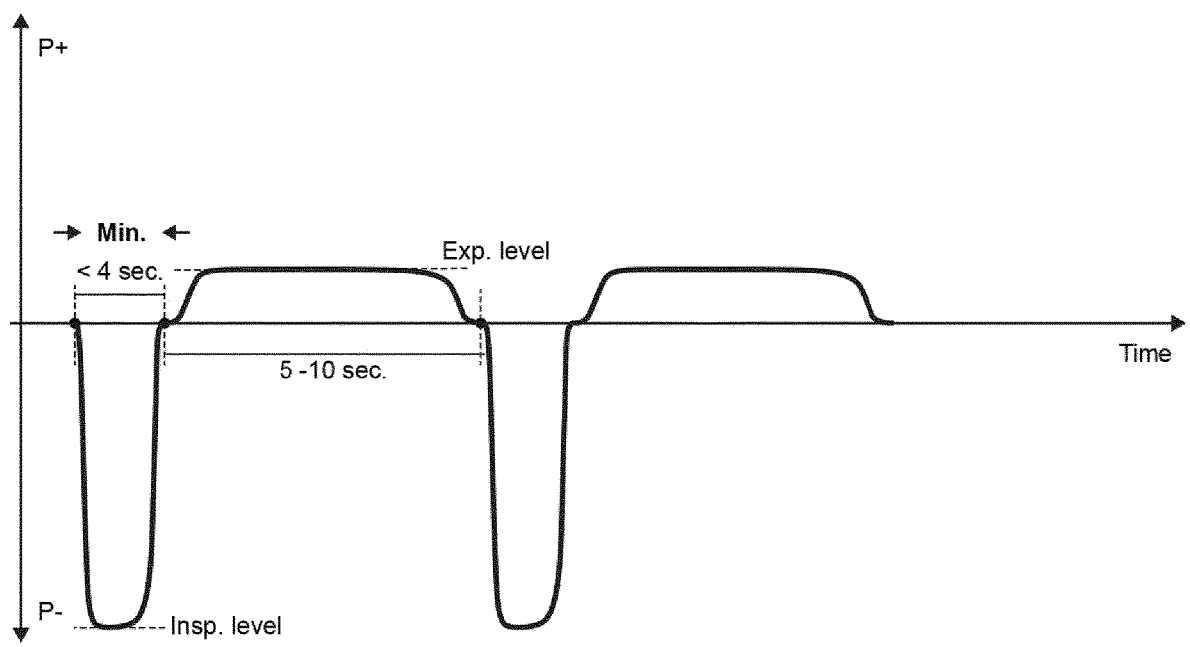
Figure 7D:
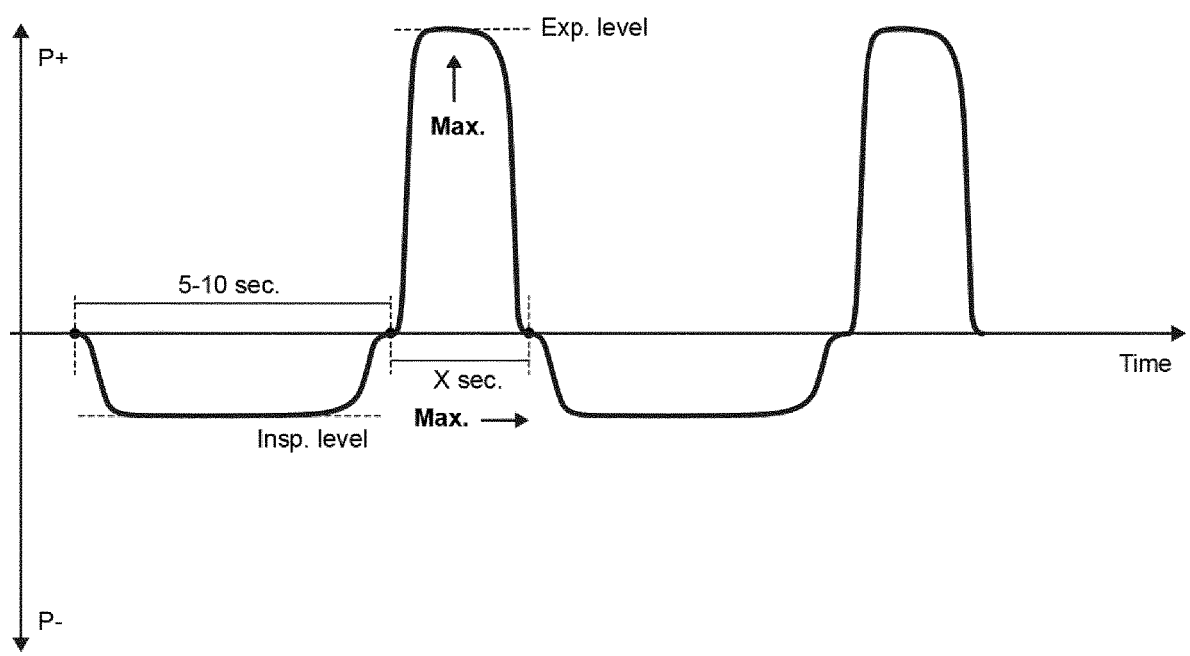
Figure 7E:
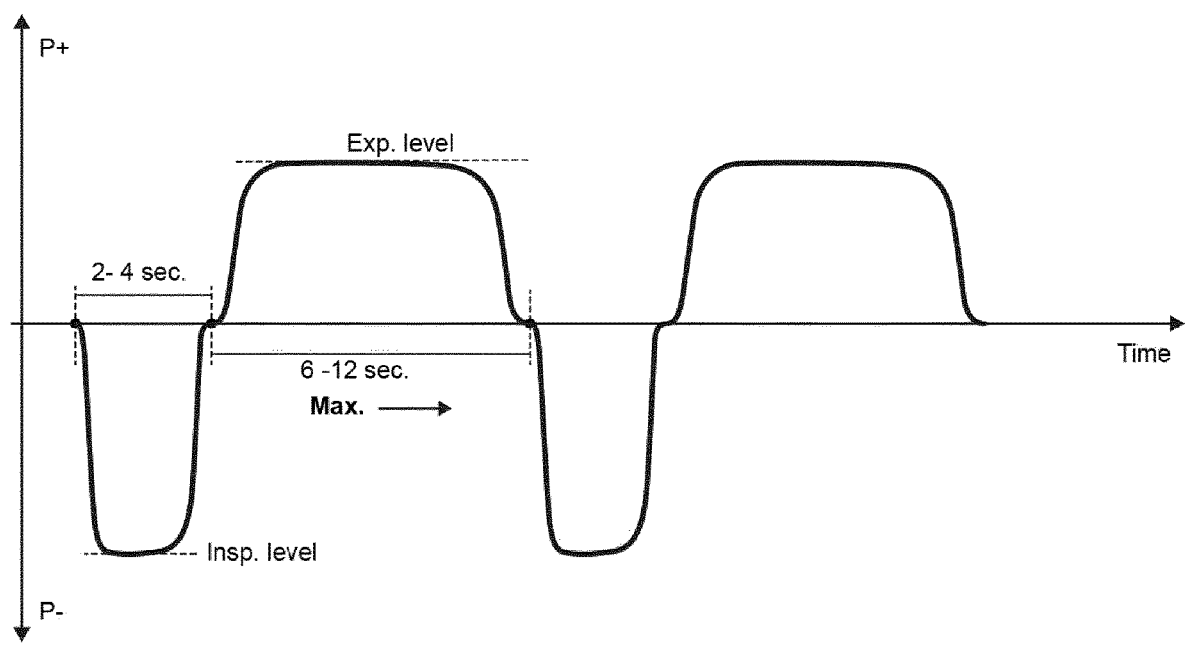
Figure 7F:
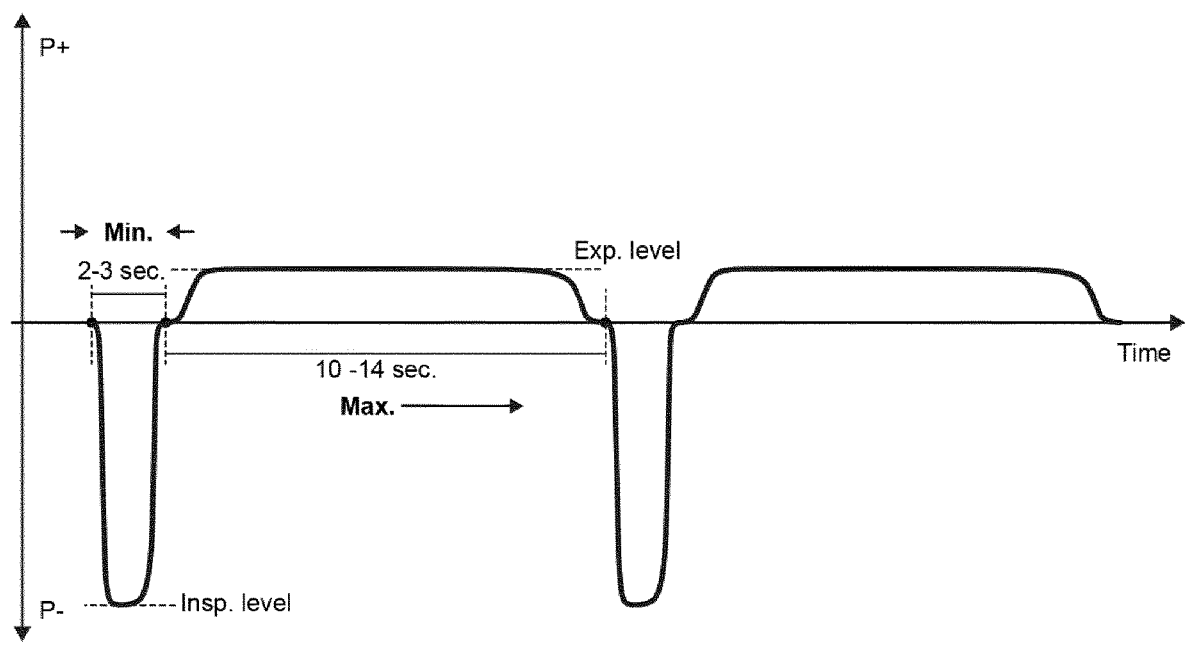

As also exemplified in FIG. 4D the housing for the breathing unit can be provided with air-way passages to the resistance units. The resistance units can then be arranged such that the air-way passages of the resistance units abut the air-way passages in the housing, respectively. The size of the air-way passages in the housing is preferably at least the size of the largest air-way passages of the resistance units. As exemplified in FIG. 4D the air-way passages of the housing and the resistance units can be arranged to directly face the breathing direction of the user such that the user inhales air directly through the inhalation air-way passage and exhales air directly into the exhalation air-way passage. With the mouthpiece located in the mouth there is preferably a very short distance from the mouth of the user to the air-way passages of the housing.

The housing is preferably sealed such that no air escapes from the housing during inhalation and exhalation of the user except through the dedicated air-way passages.

FIGS. 3-4 disclose embodiments of the breathing units. In FIG. 3, which discloses an example of a breathing unit, a mouthpiece 1 creates an airtight connection to the mouth and enables breathing through the device. The breathing unit further comprises a valve housing 2 which comprises two one-way valves 4, 5 that control the air flow so that the inhaled air passes through one adjustable resistance 4 and the exhaled air passes through another adjustable resistance 5, as also indicated by arrows in FIG. 3A. The two adjustable resistance interfaces 4, 5 may comprise predefined settings corresponding to an exact air passage clearance. The user may adjust these settings and read the setting value on the device. An electronic unit 3 is mounted on the device of FIG. 3, which may comprise a pressure meter connected to the inside of the valve housing 2. FIG. 3B shows the situation where the electronic unit 3 is dismounted from the valve housing 2. Thereby the valve housing can be cleaned thoroughly. It also makes it possible to use another valve housing with the same electronic unit 3.

FIGS. 4A-D show more detailed views of an embodiment of the presently disclosed breathing unit where the internal components can be seen. This example comprises two individually controlled air flow resistances as well as individual decoding of air resistance position. The mouthpiece 18 is formed to be held in the mouth by the user. The mouthpiece 18 enables access to an exhalation air flow way 4, an inhalation air flow way 16 and an air channel 2 to the air pressure meter. Both air flow ways in this example include one way valves 6, 6'. The device includes a housing 14 to which a detachable electronic sensor unit housing 13 can be placed and/or attached.

In the embodiment of FIG. 4 the mouthpiece 18 enables access to an exhalation air flow way 3, 4, an inhalation air flow way, 3', 4' and an air channel 2 to the air pressure sensor 12. Both air flow ways include one way valves 6, 6'.

Figure 8:
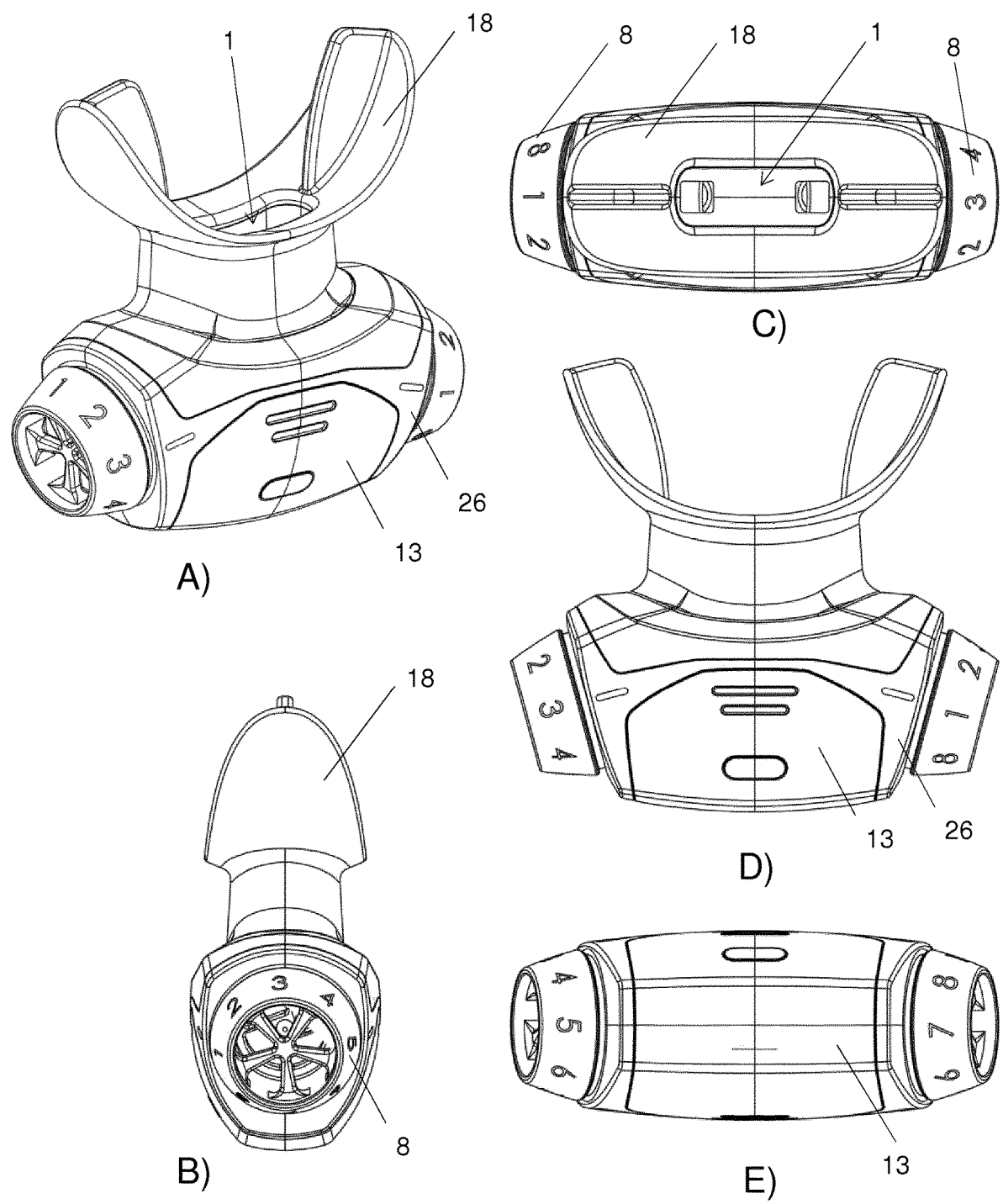
FIGS. 8A-D show different external views of an embodiment of the presently disclosed breathing unit.

Another embodiment of the breathing device with two individually controllable resistance units is shown in FIG. 8. FIG. 8 only shows outside illustrations from different view angles, where FIG. 8A is a perspective view, FIG. 8B is a side view looking directly at one of the resistance units 8, FIG. 8C is a view into the mouthpiece 18 and the mouthpiece airway 1, FIG. 8D is a top view where the detachable electronic unit 13 can be seen and FIG. 8D is a front view looking directly at the detachable electronic unit 13. The detachable electronic unit 13 is attached to the device housing 26 by means of a snap fit arrangement, such that the electronic unit 13 is solidly attached to the housing 26 during use, but can be detached for cleaning purposes.

FIG. 4C shows sensor and position indicator binary coding relation overview.

The embodiments of FIGS. 4 and 8 comprise the following enumerated parts and elements:
1. Mouthpiece airway
2. Channel to air pressure meter
3. Housing airway passage for exhalation
3'. Housing airway passage for inhalation
4. Selected airway resistance passage for exhalation
4'. Selected airway resistance passage for inhalation
5. Valve seat passage
6. One-way valve for exhalation
6'. One-way valve for inhalation
7. Position indicators on resistance dial for electronic reading
8. Resistance dial
9. Position sensors on electronic unit
10. Charging connection
11. PCB
12. Pressure sensor
13. Electronic unit housing
14. Seal
15. Battery
16. Electronic unit housing cover (for electronic sensor unit)
17. Resistance airway seal
18. Mouthpiece
19. Position indicator (sensor code 0)
20. Position indicator (sensor code 1)
26. Device housing Adjustable Air Flow Resistance, and Individual Air Flow Resistance In one embodiment of the breathing unit the least one inhalation air way has an adjustable inhalation air flow resistance, and the at least one exhalation air way has an adjustable exhalation air flow resistance. The adjustable inhalation air flow resistance and the adjustable exhalation air flow resistance may therefore be individual. The individually controlled resistances can be used for performing the following steps:
  if inhalation real-time breathing data differs from inhalation stored breathing data by more than a first predefined threshold then adjust the inhalation air flow resistance or provide guidance to a user to adjust inhalation air flow resistance, and/or
  if exhalation real-time breathing data differs from exhalation stored breathing data by more than a second predefined threshold then adjust the exhalation air flow resistance or provide guidance to a user to adjust exhalation air flow resistance.

The adjustable resistances may be for example adjustable air flow resistance setting turn buttons (8) which make it possible to adjust of the air flow resistance for the inhaled and the exhaled air. The resistance setting turn buttons may have additional settings that each corresponds to a given airway passage geometry with a known air flow resistance. The turn buttons may have a number of position stops that fix the turn button in the set position. Position of the turn button may be marked visually on the outside of the device (33).

Airway Geometry

Adjustable Cone

In one embodiment, the resistance turn buttons are mounted onto the device housing by a thread. The turn buttons may be provided with a conical form along the rotational axis that fit into matching conical openings in the housing. The conical opening has a hole in the center of the conical opening and the corresponding turn button has a number of holes that are placed around the base of the conical form. As the turn button is dialed the cone will move in and out of the conical opening allowing air to pass through the holes and through the clearance between the conical form and the conical opening hereby regulating the resistance of the air flow.

In the center of the cone form on the turn button is a hole with a predefined diameter. When the turn button is in the closed position where the two conical forms touch, the air can only pass through that hole. This may for example be used for exact measurements of the user's max inhalation and exhalation capability.

Throttle Valve

In another embodiment, the resistance turn buttons are mounted onto the device housing by a thread. The turn button has a cylindrical form matching the corresponding cylindrical hole in the device housing. The inner wall of the housing cylinder has a number of bypass-grooves extending different distances into the housing. As the button is turned the cylinder moves in or out of the housing and the bypass-grooves are either covered or exposed hereby adjusting the air flow resistance.

Disc Shaped Aperture

In yet another embodiment, the resistance turn buttons rotate on the side of the device housing. A number of apertures in the housing is placed offset from the buttons turn axis and is covered by a wall in the turn buttons. Said wall has one or more holes that can be turned in or out of alignment with the housing aperture(s) hereby adjusting the air passage and flow resistance.

There a several adjustable geometry principles that can be applied:

- One large hole in the housing matching one other hole in the turn button at a time. Each of the turn button holes has different sizes
- Multiple holes in the housing and multiple holes in the turn button. The rotational position of the turn button determines how many of the holes are aligned
- An aperture in the housing that overlap another aperture in the turn button. As the button is turned the overlap becomes smaller or larger Cylinder Wall Aperture In yet another embodiment, the resistance turn buttons have a cylindrical hollow shape that rotate inside of another cylindrical shape on the device housing. The cylindrical wall of the device housing has one or more apertures covered by the corresponding turn button cylinder. The turn button cylinder wall has one or more holes that can be turned in or out of alignment with the housing aperture hereby adjusting the air passage and flow resistance. The cylinder has an inside wall that can fit with a one way check valve.

Fixed

In yet another embodiment, a cap is placed on the inlet and outlet of the device. Each cap has a defined aperture that gives a defined air resistance.

Electronic Sensor Unit

The electronic sensor unit may comprise at least one pressure gauge for measuring air pressure in the mouthpiece. It may also comprise two separate pressure gauges for measuring air pressure in the at least one inhalation air way and the at least one exhalation air way. The electronic sensor unit may further comprise air resistance setting detectors and/or a time counter and/or a wireless transmitter for continuously transmitting air pressure data in real-time.

Detachable Sensor Measuring Unit

The electronic sensor unit may be detachable from the breathing unit. In one embodiment the at least one pressure gauge for measuring air pressure is incorporated in the detachable electronic sensor unit. The detachable electronic sensor unit may further comprise two air resistance setting detectors for determining positions of the adjustable inhalation air flow resistance and adjustable exhalation air flow resistance. In such a configuration, one resistance setting detector may be associated with the adjustable inhalation air flow resistance and the other resistance setting detector may be associated with the adjustable exhalation air flow resistance.

In one embodiment the electronic sensor unit is detachably mounted to a housing of the breathing unit. The electronic sensor unit may have its' own housing which can then be detachably connected to the housing of the breathing unit, preferably such that the sensors are directly operative upon insertion (attachment) of the electronic sensor unit to the breathing unit or the housing of the breathing unit.

In one embodiment the breathing unit further comprises a pressure airway, wherein the pressure airway is configured to connect an inner volume of the breathing unit with the at least one pressure gauge. This is exemplified in FIG. 4D.

In one embodiment the electronic sensor unit is in the form of a cassette which accommodates all electronic parts of the breathing unit. The cassette may be attached from the top side of the breathing device, i.e. opposite to the mouthpiece, as exemplified in FIG. 3B. This attachment is preferably airtight, i.e. no air is escaping through this connection. The pressure gauge in the sensor unit can then advantageously be mounted in the sensor unit but close to one end of the air pressure way. Even though the airtight connection isolates the air pressure gauge from the air pressure way, the air pressure gauge can then still sense changes in the air pressure. E.g. atmospheric pressure can be equilibrium and positive and negative pressure in the air pressure way coming from exhalation and inhalation by the user can then be sensed by the air pressure gauge, thereby sensing the relative air pressure.

A detachable sensor measuring unit is also an advantage in relation to cleaning of the device. When the electronic sensor unit is detached from the rest of the breathing unit, the rest of the breathing unit may be washed in water since the electronic sensor unit may be designed to accommodate all electronic parts of the device. The solution thereby provides a device that can be more efficiently cleaned.

Different means for attaching and detaching the electronic sensor unit to/from the breathing unit are possible. In one embodiment the detachable electronic sensor unit comprises means for snap-fitting to the breathing unit. The detachable electronic sensor unit may thereby comprise one part of a snap connection, such as a male part, and the main unit comprises another part of the snap connection, such as a female part. Alternatively, or in combination, the detachable electronic sensor unit may comprise a mounting clip for mounting the electronic unit to the breathing unit.

Electronic Reading of Air Flow Resistance Position

A further aspect of the presently disclosed respiratory device and system for exercising and analysing respiration of a subject relates to the possibility to read the air flow resistances, in particular to read it electronically from the electronic sensor unit. Therefore the positions of the air flow resistance settings may be monitored by the electronics resistances. The position detecting geometry may be constructed in various ways.

In one embodiment the breathing unit comprises sensors for reading the positions of the adjustable inhalation air flow resistance and adjustable exhalation air flow resistance. The sensors may be magnetic sensors wherein the adjustable inhalation air flow resistance and adjustable exhalation air flow resistance are provided with magnets. In one embodiment the magnetic sensors are provided outside a circular circumference of the flow resistance setting turn buttons, thereby indicating a position of a magnet on the turn button. The sensors may be arranged to determine the rotational position of the turn button(s).

FIG. 5 shows an example of the reading of air flow resistance positions. The sensors and actuators (magnets) may have a number of combinations to provide information regarding the position of the turn button(s) as shown in FIG. 5. FIG. 4C shows an overview of an example of sensor and position indicator binary coding relation. The embodiment of FIG. 5 comprises the following components:

1.-8. Resistance dial positions
9. Position indicator (sensor code 0)
10. Position indicator (sensor code 1)
11. The three position indicators in reading position for this resistance dial setting
12. Sensors ABC
13. Resistance dial The electronic reading of air flow resistance position may involve different elements and component for the realization of such functionality:

Magnetic Response
In one embodiment, small magnets are placed around the rotational axis of the resistance settings turn button in binary coded positions. The electronic sensor unit situated in close proximity is fitted with a number (n) of hall magnetic sensors. Each sensor can detect if a magnet is positioned close by or not, hereby the electronic sensor unit can detect the rotational position of the resistance settings turn button E.g. if the number of sensors are three, eight different positions can be identified.

Magnetic Inductance
In another embodiment, small metal pieces are placed around the rotational axis of the resistance settings turn button in binary coded positions. The electronic sensor unit situated in close proximity is fitted with a number (n) of metal sensors. Each sensor can detect if a metal piece is positioned close by or not, hereby the electronic sensor unit can detect the rotational position of the resistance settings turn button E.g. if the number of sensors are three, eight different positions can be identified.

Light Reflection
In yet another embodiment, along the outer line of the inner side of the resistance settings turn button, the button is marked with different gray tones. A light source sets light on the gray marked area in front of a single light intensity sensor. The measurement can be used by the electronics to identify the position of the resistance settings turn button.

Encoder
In yet another embodiment, along the outer line of the inner side of the resistance settings turn button, the button is marked with a number of binary coded black/white fields (circles). These are all lighted by a light source and each of them can be separately read by a number of light intensity sensors. E.g. if the number of sensors are three, eight different positions can be identified.

Electrical Capacity
In yet another embodiment, along the outer line of the inner side of the resistance settings turn button, the button has metal plates of different sizes, one for each position setting. The difference in electrical capacity can then be read by the electronics, to identify the position of the resistance settings turn button.

Electronic Respiratory Air Pressure Measurement
In the respiratory air flow housing, an electronic air pressure module may be provided that is configured to measure pressure of both inspiratory air flow and expiratory air flow. The electronic air pressure module may be part of the electronic unit that may be detachable from the breathing as described above. The air pressure measurement may be constructed in a number of different ways. In the following a number of examples are described in more detail.

Absolute Pressure Measurement
In one embodiment, the air flow is guided into an air tight channel where the absolute air pressure can be measured in the housing of the air flow.

Relative Pressure Measurement
In another embodiment, the air flow is guided into an air channel which has been pressure neutralized to the ambient atmospheric pressure. The relative air pressure can then be measured in the housing of the air flow, e.g. in the air pressure way as described elsewhere.

Sealed Enclosure
In yet another embodiment, the air channel for the air flow pressure is sealed by a flexible membrane which transfers the air pressure into the air pressure measurement unit.

Separated Enclosure
In yet another embodiment, the air channel for the air flow pressure is located as a side channel from the direct air flow. The side channel transfers the air pressure into the air pressure measurement unit.

Communication
The breathing unit may comprise a communication unit comprising a transmitter, preferably a wireless transmitter, such as a Bluetooth or wifi or the like, for transmitting, preferably continuously transmitting, air pressure data in real-time or substantially real-time. The communication unit/transmitter may be located in the electronic sensor unit. Such a communication unit can communicate settings data, measured data and calculated data with common device platforms through commonly known communication protocols. Settings data can then be returned to the device. Settings data may comprise device ID and air flow resistance settings. Measured data may comprise data of exercise session air pressures and duration. Calculated data may comprise data of air flow rate, respiratory tract volume, respiratory muscle strength and respiratory muscle explosive strength.

Software Application

The presently disclosed respiratory system may comprise a software application executable on a remote device and configured for executing the steps of:

- continuously receiving said air pressure data via a receiver on the remote device,
- processing the air pressure data by means of the remote device to provide real-time breathing data representing inhaled air pressure, inhaled air flow rate, exhaled air pressure, exhaled air flow rate and one or more of: inhaled respiratory tract volume, exhaled respiratory tract volume, inhaled respiratory muscle strength, exhaled respiratory muscle strength, inhaled respiratory muscle explosive strength (hældning) and exhaled respiratory muscle explosive strength,
- displaying at least a part of the real-time breathing data on a screen of the remote device,
- comparing real-time breathing data to stored breathing data of a predefined personal breathing routine.

The computer software may be arranged to, when executed, provide functionality corresponding to a calculation unit, an analyzing unit and/or a recommendation unit and/or provider of a user profile and/or provider of historical data. The following section describes possible functioning of the calculation unit, the analysing unit and the recommendation unit.

Calculation Unit

The electronic unit may comprise an electronic calculation unit, e.g. a processing unit, configured for collecting input from the electronic sensor unit. Processing and/or collection of data from the electronic sensor unit may also be provided by means of an external/remote device, such as a smartphone or other similar device, receiving the transmitted data. E.g. by means of the software application as described above.

From the measurement of air flow resistance, respiratory air pressure and/or time, a number of respiratory related data can be derived as shown in FIG. 6. The calculated data may be relevant to the various user profiles.

The respiratory air flow rate (I/sec) may be calculated from air flow resistance and air pressure, e.g. the system can be calibrated to measure and calculate the respiratory air flow rate for a given resistance and air pressure.

The respiratory tract volume (I) may be calculated from air flow resistance, air pressure and duration of respiration, for example as shown in FIG. 6 corresponding to the areas indicated with reference numerals 2 and 5.

The inhaled and exhaled respiratory muscle strength (hPa) may be calculated from the minimum and maximum air pressure, respectively, as exemplified in FIG. 6, reference numerals indicating levels 3 and 6. Duration of inspiration, maximum expiratory air pressure and duration of expiration may further be calculated.

The respiratory explosive muscle strength (hPa/sec)—also known as Rate of force Development RFD—may be calculated from the change of inspiratory/expiratory air pressure in time, i.e. the slope of the curve, as exemplified in FIG. 6, reference numerals 1 and 4.

Analysing Unit

The system may further comprise an electronic analyzing unit which collects input from the electronic sensor unit and from the electronic calculation unit. This analysis may also be provided by means of an external/remote device, such as a smartphone or other similar device, e.g. by means of the software application as described above.

The measured and derived respiratory data may be used to analyze the respiratory condition during and after the exercise session.

The breathing pattern may represent the inspiratory and expiratory air pressure as a function of time during exercise session. Results may be analyzed as average inspiratory air pressure, average expiratory air pressure, and breathing stability. FIG. 7 (A)-(F) show 6 examples of breathing patterns.

Maximum air pressures may be the minimum inspiratory and maximum expiratory air pressures as a function of the exercise session. Results may be compared to previous exercise sessions.

The respiratory tract volume pattern may be represented by the respiratory tract volume as a function of time during exercise session. Results may be compared to previous exercise sessions.

The respiratory muscle strength pattern may be the respiratory muscle strength as a function of time during exercise session. Results may be compared to previous exercise sessions.

The respiratory muscle explosive strength pattern may be the respiratory muscle explosive strength as a function of time during exercise session. Results may be compared to previous exercise sessions.

Recommendation Unit

The system may further comprise an electronic recommendation unit arranged to collect input from the electronic sensor unit, from the electronic calculation unit and from the electronic analyzing unit. This recommendation analysis may also be provided by means of an external/remote device, such as a smartphone or other similar device, e.g. by means of the software application as described above.

The analysis of respiratory data may be used to recommend exercise sessions for the improvement of the respiratory condition. The recommendation may be provided to various exercise profiles.

The exercise session parameters may be settings of inspiratory air resistance, expiratory air resistance, duration of inspiratory session, duration of expiratory session, and total session time. Recommendations of default parameters may be set according to the user profile.

The recommendation of exercise session parameters may be derived from historical measured, derived and analyzed respiratory data. Recommendations of parameters may be set according to the user profile.

EXAMPLES

The following section describes additional features and applications of the presently disclosed respiratory system. The functions are exemplary and intended to illustrate possible applications and are not to be construed as limiting to the presently disclosed invention:

Example: User Interactive Dynamic Training Session Parameters

The respiratory exerciser and analyzer recommend a set of dynamic training session parameters. The parameters include duration, training level, changes, and intensity. The system gives continuous feed-back of the user's performance in relation to the predefined parameters. The system dynamically changes the training system parameters during training according to the real-time performance. This can be for a single training session or for a sequence of training sessions.

Example: Gamification

The feed-back is presented to the user as a motivating virtual game. For instance an encouraging setup with gaining points or diplomas according to progress.

Example: Virtual Tour

The training session is exemplified to the user as a simulated journey.

Example: Sport Simulation

The training session is exemplified as real sport endurance, such as a swimming session, where you have limited access to breathing between strokes, or a bike route with dynamic intensity exemplified with up- and down hills.

Example: Compete and Compare

The respiratory exerciser and analyzer gives the user the ability to compete and/or compare with other users in real-time or using historical training session data.

Example: Point System

Each user acquires points according to performance of a specific training program and can compare to other users.

Example: User Group Training

Each user acquires points according to performance of a specific training program and can compare to other users in a closed group. For example a sports club or other user groups virtual or physical.

Example: Follow the Pro's

The training session is exemplified as a possibility for the user to follow a favorite athlete in their specific or recommended training program.

Further Details of the Invention

The invention will now be described in further detail with reference to the following items:

1. A respiratory exerciser and analyzer comprising
   a breathing device with a mouthpiece and separate air flow inhalation and exhalation tubes with individually adjustable air flow resistances,
   an electronic sensor unit, providing measurement of inhaled air pressure, exhaled air pressure, duration of inhalation, duration of exhalation and air flow resistance settings,
   an electronic calculation unit, providing calculated data of inhaled air flow rate, exhaled air flow rate, respiratory tract volume, respiratory muscle strength and respiratory muscle explosive strength, and/or
   an electronic analyzing unit, providing respiratory condition patterns data of breathing, maximum air pressure, respiratory tract volume and respiratory muscle strength, and/or
   an electronic recommendation unit, providing data of recommended exercise sessions, set in accordance with the user profile, and/or
   an electronic communication unit, providing data interchange with a computer, a tablet, a smartphone, a separate device and a cloud based server, and, optionally
   a software application providing exercise data storage, data analyzing, session recommendations, and setup on a computer, a tablet, a smartphone, a separate device and a cloud based server.
2. The respiratory exerciser and analyzer of item 1, wherein an electronic unit analyzes the breathing pattern from the data of air pressure and exercise duration, and/or
   wherein an electronic unit analyzes the maximum air pressure pattern from the data of air pressure and exercise duration, and/or
   wherein an electronic unit analyzes the respiratory tract volume pattern from the data of respiratory tract volume and exercise duration, and/or
   wherein an electronic unit analyzes the respiratory muscle strength pattern from the data of respiratory muscle strength and exercise duration, and/or
   wherein an electronic unit analyzes the respiratory muscle explosive strength pattern from the data of respiratory muscle explosive strength and exercise duration, and/or
   wherein a performance status is provided in order to track training progression.
3. The respiratory exerciser and analyzer of any of the preceding items, wherein an electronic unit calculates the air flow rate from the measured data of air pressure and air flow resistance, and/or
   wherein an electronic unit calculates the respiratory tract volume from the data of air pressure, air flow resistance and air flow duration, and/or
   wherein an electronic unit calculates the respiratory muscle strength from the data of air pressure, and/or
   wherein an electronic unit calculates the respiratory muscle explosive strength from the data of change of air pressure in time, and/or
   user real time feed-back compared with previous measurements is provided.
4. The respiratory exerciser and analyzer any of the preceding items, wherein an electronic unit recommends default exercise session parameters for the improvement of the respiratory condition from the data of the user profile, and/or wherein an electronic unit recommends exercise session parameters for the improvement of the respiratory condition from the data of respiration measurements, calculations and analyzes of inhalation/exhalation data together with data from the user profile.
5. The respiratory exerciser and analyzer of any of the preceding items arranged to recommend a set of dynamic training session parameters and gives continuous feed-back, and/or wherein the feed-back is presented to the user as a motivating virtual game, and/or arranged to dynamically change the training system parameters during training according to the real-time performance for a single training or for a sequence of sessions.
6. The respiratory exerciser and analyzer of any of the preceding items, arranged to give the user the ability to compete and/or compare with other users in real-time or using historical training session data.
7. The respiratory exerciser and analyzer of any of the preceding items, wherein the air flow resistance setting is detected by an electronic unit.

8. The respiratory exerciser and analyzer of any of the preceding items, wherein

The invention claimed is:

1. A respiratory system for exercising and analyzing respiration of a user, the respiratory system comprising:
a breathing unit comprising:
a housing comprising an inhalation passageway, an exhalation passageway, and a pressure channel, wherein the pressure channel is separate from the inhalation passageway and the exhalation passageway;
a mouthpiece connected to the housing, the mouthpiece comprising a mouthpiece airway that is in fluid communication with the inhalation passageway, the exhalation passageway, and the pressure channel, wherein the mouthpiece airway is fluidly connected to:
at least one inhalation airway having an adjustable inhalation air flow resistance via the inhalation passageway in the housing, and
at least one exhalation airway having an adjustable exhalation air flow resistance via the exhalation passageway in the housing,
wherein the adjustable inhalation air flow resistance and the adjustable exhalation air flow resistance are separate and configured to operate independently of each other; and
an electronic sensor unit attachable to the housing, comprising:
at least one pressure sensor in direct fluid communication with the pressure channel of the housing for measuring air pressure in the mouthpiece airway of the mouthpiece, and
a processing unit for at least one of collecting, storing or transmitting air pressure data.

2. The respiratory system according to claim 1, wherein the electronic sensor unit further comprises a wireless transmitter for continuously transmitting the air pressure data in real-time.

3. The respiratory system according to claim 1, further comprising a software application executable on a remote device and configured for executing the steps of:
continuously receiving said air pressure data via a receiver on the remote device,
processing the air pressure data by using the remote device to provide real-time breathing data representing inhaled air pressure, inhaled air flow rate, exhaled air pressure, exhaled air flow rate and one or more of: inhaled respiratory tract volume, exhaled respiratory tract volume, inhaled respiratory muscle strength, exhaled respiratory muscle strength, inhaled respiratory muscle explosive strength and exhaled respiratory muscle explosive strength;
displaying at least a part of the real-time breathing data on a screen of the remote device; and
comparing the real-time breathing data to stored breathing data of a predefined personal breathing routine.

4. The respiratory system according to claim 3, wherein the software application is further configured for executing the steps of:
if inhalation real-time breathing data differs from inhalation stored breathing data by more than a first predefined threshold then adjust the adjustable inhalation air flow resistance or provide guidance to the user to adjust the adjustable inhalation air flow resistance; and/or
if exhalation real-time breathing data differs from exhalation stored breathing data by more than a second predefined threshold then adjust the adjustable exhalation air flow resistance or provide guidance to the user to adjust the adjustable exhalation air flow resistance.

5. The respiratory system according to claim 1, wherein the adjustable inhalation air flow resistance and the adjustable exhalation air flow resistance are respectively adjustable air flow resistance setting turn buttons.

6. The respiratory system according to claim 1, wherein the at least one pressure sensor is arranged to measure inhaled air pressure and exhaled air pressure.

7. The respiratory system according to claim 1, wherein the electronic sensor unit is detachable from the housing unit.

8. The respiratory system according to claim 7, wherein the at least one pressure sensor for measuring the air pressure is incorporated in the electronic sensor unit.

9. The respiratory system according to claim 7, wherein the electronic sensor unit further comprises two air resistance setting detectors and wherein one of the two air resistance setting detectors is associated with the adjustable inhalation air flow resistance and the other of the two air resistance setting detectors is associated with the adjustable exhalation air flow resistance.

10. The respiratory system according to claim 7, wherein the electronic sensor unit is detachably mounted to the housing of the breathing unit.

11. The respiratory system according to claim 7, wherein an attachment connection between the mouthpiece and the electronic sensor unit is airtight.

12. The respiratory system according to claim 7, wherein the electronic sensor unit is a cassette accommodating all electronic parts of the breathing unit.

13. The respiratory system according to claim 7, wherein the at least one pressure sensor is located in the electronic sensor unit and configured to measure a relative air pressure in the pressure channel.

14. The respiratory system according to claim 7, wherein the electronic sensor unit is configured for snap-fitting to the housing and wherein the electronic sensor unit comprises one part of a snap connection and the housing comprises another part of the snap connection.

15. The respiratory system according to claim 7, wherein the mouthpiece is washable in water in a configuration wherein the electronic sensor unit is detached and excluded from the mouthpiece.

16. The respiratory system according to claim 1, wherein the breathing unit comprises sensors for reading positions of the adjustable inhalation air flow resistance and the adjustable exhalation air flow resistance.

17. The respiratory system according to claim 16, wherein the sensors for reading the positions are magnetic sensors and wherein the adjustable inhalation air flow resistance and the adjustable exhalation air flow resistance are provided with magnets.

18. The respiratory system according to claim 17, wherein the adjustable inhalation air flow resistance and the adjustable exhalation air flow resistance are respectively adjustable air flow resistance setting turn buttons provided with the magnets, and wherein the magnetic sensors are provided outside a circular circumference of each of the adjustable air flow resistance setting turn buttons, thereby respectively indicating positions of the magnets on the corresponding adjustable air flow resistance setting turn button.

19. The respiratory system according to claim 17, wherein the adjustable inhalation air flow resistance and the adjustable exhalation air flow resistance are respectively adjustable air flow resistance setting turn buttons provided with the magnets, and wherein the magnetic sensors are arranged to determine a rotational position of the adjustable air flow resistance setting turn buttons.

20. The respiratory system according to claim 1, wherein said at least one pressure sensor is located external to the pressure channel, the at least one inhalation airway, and the at least one exhalation airway exhalation air way.

21. The respiratory system according to claim 1, wherein the pressure channel is provided between the inhalation passageway and the exhalation passageway.

22. The respiratory system according to claim 21, wherein the pressure channel is provided between the at least one inhalation airway and the at least one exhalation airway.

23. The respiratory system according to claim 1, wherein the mouthpiece and the electronic sensor unit are attached at opposite ends of the housing and at opposite ends of the pressure channel.

24. The respiratory system according to claim 1, wherein the mouthpiece includes a breathing opening that is in fluid communication with the mouthpiece airway and faces a breathing direction of the user, wherein the pressure channel, the inhalation passageway, and the exhalation passageway face the breathing direction of the user.

25. The respiratory system according to claim 1, wherein the mouthpiece includes a breathing opening that is in fluid communication with the mouthpiece airway and faces a breathing direction of the user, wherein the pressure channel extends in a same direction as the breathing direction and is centered with respect to the mouthpiece airway and the breathing opening.

* * * * *